United States Patent [19]

Ptacek et al.

[11] Patent Number: 5,373,197

[45] Date of Patent: Dec. 13, 1994

[54] HIGH VOLTAGE DUAL OUTPUT LABORATORY POWER SUPPLY

[75] Inventors: James F. Ptacek, Kansas City; Karmon D. Almquist, Buckner; Robert R. Vetter, Shawnee Mission; John L. Aker, Kansas City, all of Mo.

[73] Assignee: Labconco Corporation, Kansas City, Mo.

[21] Appl. No.: 970,065

[22] Filed: Nov. 2, 1992

[51] Int. Cl.$^5$ ................................................ H02J 3/00
[52] U.S. Cl. ........................................ 307/52; 307/31; 307/38
[58] Field of Search ................. 307/18, 21, 22, 25, 307/26, 31, 32, 33, 35, 43, 52, 53, 56, 38, 39, 40

[56] References Cited

U.S. PATENT DOCUMENTS

| | | |
|---|---|---|
| 4,157,499 | 6/1979 | Kacerek . |
| 4,612,106 | 9/1986 | Kromer et al. . |
| 4,630,220 | 12/1986 | Peckinpaugh ............... 307/31 |
| 4,668,362 | 5/1987 | November et al. . |
| 4,808,841 | 2/1989 | Ito et al. ....................... 307/38 |
| 5,170,068 | 12/1992 | Kwiatkowski et al. ....... 307/31 |

OTHER PUBLICATIONS

Buchler Instruments, Power Supplies Instruction Manual, 1990, A. Labconco Co., Fairfield, N.J. 07004-1615.

Primary Examiner—Jeffrey A. Gaffin
Attorney, Agent, or Firm—Shook, Hardy & Bacon

[57] ABSTRACT

A microprocessor-controlled power supply with substantially independent high voltage outputs monitors and regulates two separate electrophoresis applications running simultaneously. The software associated with the dual output power supply provides independent control of each application, including automatic crossover between control parameters within each application. After parameter values are selected for each application and the applications are initiated, the software monitors the actual parameter values with relation to the selected values and adjusts the actual value of the controlling parameter for each initiated application to maintain the actual parameter values within the selected parameter values.

19 Claims, 5 Drawing Sheets

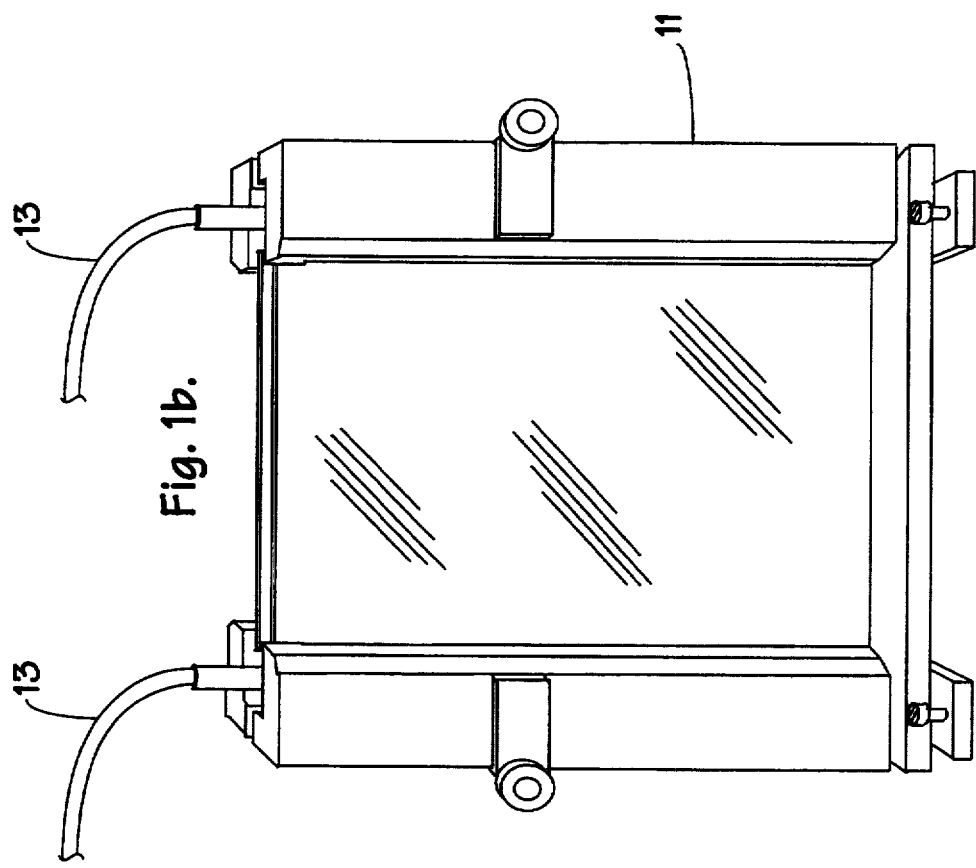
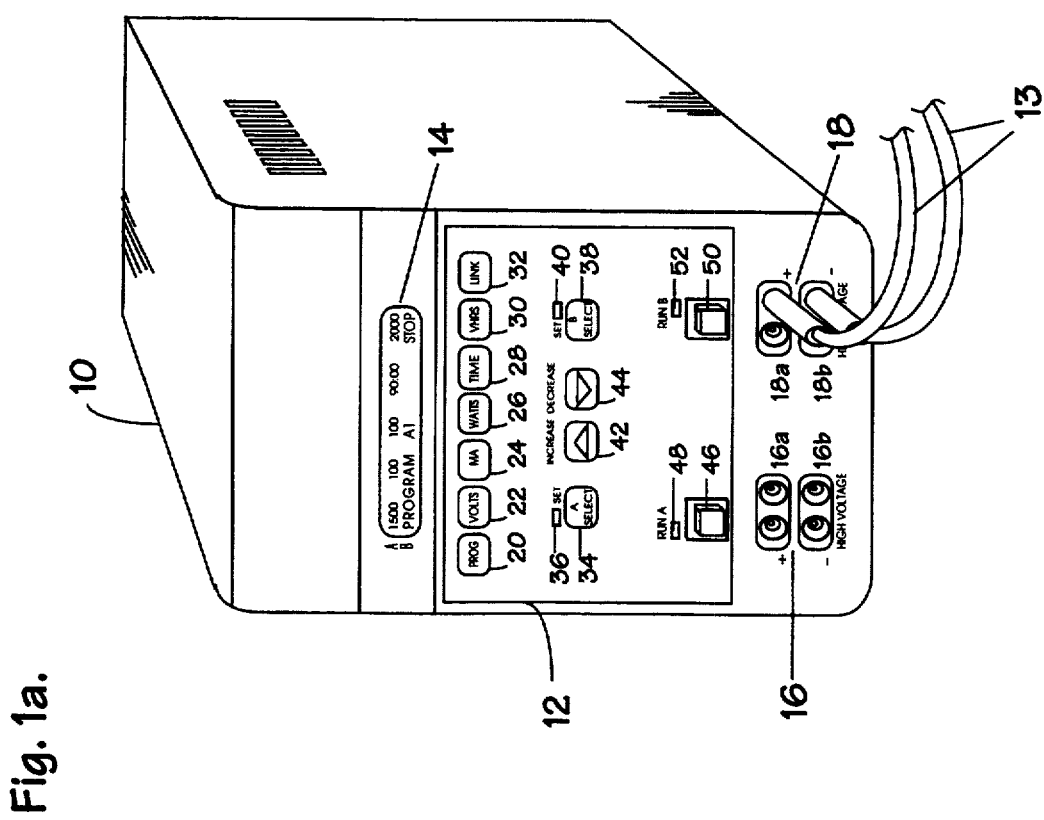

HIGH VOLTAGE DUAL OUTPUT LABORATORY POWER SUPPLY

BACKGROUND OF THE INVENTION

This invention relates to a high voltage power supply for laboratory applications and, more particularly, to a dual output power supply for monitoring and controlling two electrophoresis experiments at the same time.

Electrophoresis is a separation method involving the movement of charged molecules in an electrical field. The electrophoresis process occurs in a laboratory appliance such as a supporting medium or gel. The gel reduces the distorting effects of diffusion and helps to further separate the moving molecules. Most electrophoresis apparatus provide two buffer chambers. The gel is positioned so that each end is in one of the buffer chambers with the gel being the only connection between them. The leads from the buffer chambers are connected to a power supply, and an electrical field is created when the power is applied. In the electrical field, one buffer is the cathode and the other buffer is the anode. Thus, any sample applied on the gel will move according to its charge. U.S. Pat. No. 4,612,106 relates to the field of electrophoresis and is hereby incorporated by reference.

A known single output power supply, such as catalog number 433-3300 manufactured by Buchler Instruments Division, Labconco Corporation, Kansas City, Mo., can monitor and control a single electrophoresis experiment. However, to monitor and control two electrophoresis experiments at the same time, a second single output power supply must be utilized.

The known single output power supply, referenced above, utilizes a microprocessor to control the application. Specifically, the microprocessor stores selected parameter values and monitors the actual parameter values as the application is executed. Accordingly, the actual parameter values are adjusted if they exceed the selected values.

For many applications, a single parameter such as voltage is selected to control the entire experiment. Then, by selecting the desired voltage and the maximum values for the other parameters, the application will operate at constant voltage. However, if the maximum capacity of the power supply is exceeded for current or power, the application will operate at a reduced voltage.

The known single output power supply also allows for crossover between parameters. That is, if voltage is the controlling parameter and the selected maximum value for either milliamps or watts is exceeded by the actual value, then the power supply will automatically cross over to constant current or constant power as the controlling parameter. This crossover feature is especially useful during an electrophoresis experiment because the gel's resistance typically decreases over the course of the experiment. Thus, when voltage is controlling, the current and wattage values rise because they are proportional to resistance.

The primary disadvantage of the known single output power supply is inefficiency. Prior to the present invention, each additional application required an additional single output power supply. Otherwise, the applications must be conducted one after the other. Typically, a single electrophoresis experiment will last from one to eighteen hours. Consequently, running two or more independent applications with a single output power supply requires either the added space and expense of providing additional power supplies, or the inconvenience of running the applications consecutively, which consumes considerably more time than running the applications concurrently.

SUMMARY OF THE INVENTION

Accordingly, it is an important object of the present invention to provide a novel method and apparatus that can control two separate laboratory applications at the same time. The present invention improves the state of the art by dramatically increasing efficiency. The dual output power supply is approximately the same size as a conventional single output power supply; thus, it saves space as well as time when running two applications concurrently.

It is a further object of the present invention to provide a novel method and apparatus that will compare the various parameter values of electrically coupled electrophoresis applications, both individually and collectively, and adjust said parameter values to remain within maximum parameter constraints. For example, the sum of the watts values of all electrically coupled electrophoresis applications must not exceed a-certain value, and other parameter values for the various applications may be adjusted to prevent an excessive accumulative watts value.

Furthermore, the present invention eliminates significant portions of the software and hardware that are duplicated when using two single output power supplies. The dual output power supply requires only one user interface and one outer housing, and the software can be written such that one program to control two separate applications is more efficient than two separate programs, each controlling one application.

BRIEF DESCRIPTION OF THE DRAWINGS

FIG. 1a is a perspective view of a preferred embodiment of the present invention adopted to be coupled with an electrophoresis appliance.

FIG. 1b is a perspective view of an electrophoresis appliance adapted to be coupled with the embodiment of the present invention in FIG. 1a.

FIG. 2 is a computer program flow chart for operation on the embodiment of the present invention in FIG. 1a.

FIG. 4 is a schematic representation of the electrical connections for the controller board in accordance with the embodiment of the present invention in FIG. 1a.

FIG. 5 is a schematic representation of the electrical connections for the high voltage boards in accordance with the embodiment of the present invention in FIG. 1a.

DETAILED DESCRIPTION OF THE PREFERRED EMBODIMENT

Figure 2:
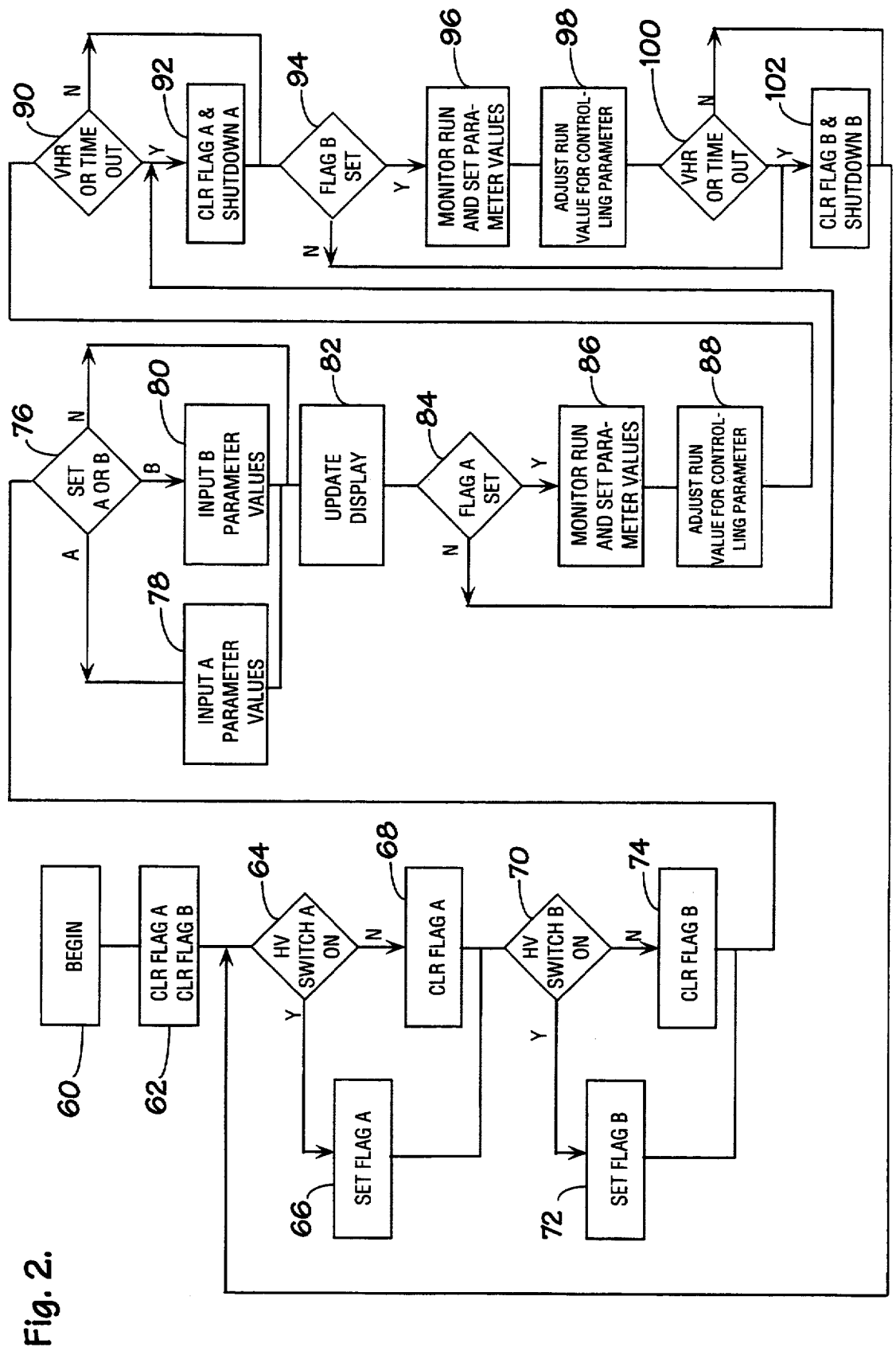

Referring initially to FIG. 1a, dual power supply unit 10 is coupled with electrophoresis appliance 11 by leads 13. Electrophoresis appliance 11 may be similar to any one of a variety of units described in Labconco Corporation's catalog, *Electrophoresis and Separations Technology Products*. The particular appliance shown in FIG. 1a is the vertical slab. Dual power supply unit 10 includes a single user interface 12, a liquid crystal display 14, and two electrical outlets: high voltage output 16, and first high voltage output 18. In this embodiment, user interface 12 includes seven parameter switches. The program switch 20 is used to select program numbers A1 through A5, corresponding to first output 16, and B1 through B5, corresponding to second output 18, when in SET mode. The program number is indicated on display 14 when in SET mode, and blinks when program switch 20 is depressed. Volts switch 22, milliamps switch 24, watts switch 26, time switch 28, and volt-hours switch 30 are used in SET mode to select the appropriate maximum value or limit for each parameter. Link switch 32 toggles between LINK and STOP to select whether to automatically link two or more programs together when in SET mode. A Select switch 34 initiates SET mode for side A (which corresponds to first output 16), and it causes display 14 to alternate between SET limits and actual operating values for the A power supply during RUN mode. Light emitting diode (LED) 36, corresponding to and positioned above A Select switch 34, indicates when side A of the unit is in SET mode. Likewise, B Select switch 38 initiates SET mode for side B, (which corresponds to second output 18) and it causes display 14 to alternate between SET limits and actual operating values for the B power supply during RUN mode. LED 40, corresponding to and positioned above B Select switch 38, indicates when side B of the unit is in SET mode. Increase button 42 and decrease button 44 are used to increase or decrease the values corresponding all of the parameter switches except link/stop switch 32.

When an application is placed in RUN mode, it becomes an initiated application. Run A switch 46 toggles high voltage switch A and provides high voltage at a first high voltage output 16, corresponding to side A. LED 48, corresponding to and positioned above Run A switch 46, indicates when a program is running on side A. Similarly, Run B switch 50 toggles high voltage switch B and provides high voltage at a second high voltage output 18, corresponding to side B, and LED 52, corresponding to and positioned above Run B switch 50, indicates when a program is running on side B.

Display 14 indicates the SET parameters for power supply A or B when in SET mode. In the RUN mode, display 14 can indicate the actual operating parameters for both supplies at the same time.

Output 16 has at least one positive terminal 16a and negative terminal 16b. Similarly, output 18 has at least one positive terminal 18a and negative terminal 18b. In a preferred embodiment, output 16 and output 18 each have two sets of positive and negative terminals, although an output with three or more sets of terminals for each side of the power supply is contemplated by the present invention. The characteristics of the positive and negative terminals comprising output 16 are essentially identical; however, the positive and negative terminals comprising output 16 are substantially independent from the positive and negative terminals comprising output 18. Accordingly, this multi-terminal outlet feature further increases the efficiency of the present invention because a set of identical applications may run on output 16 while a different set of identical applications run on output 18.

Figure 3:
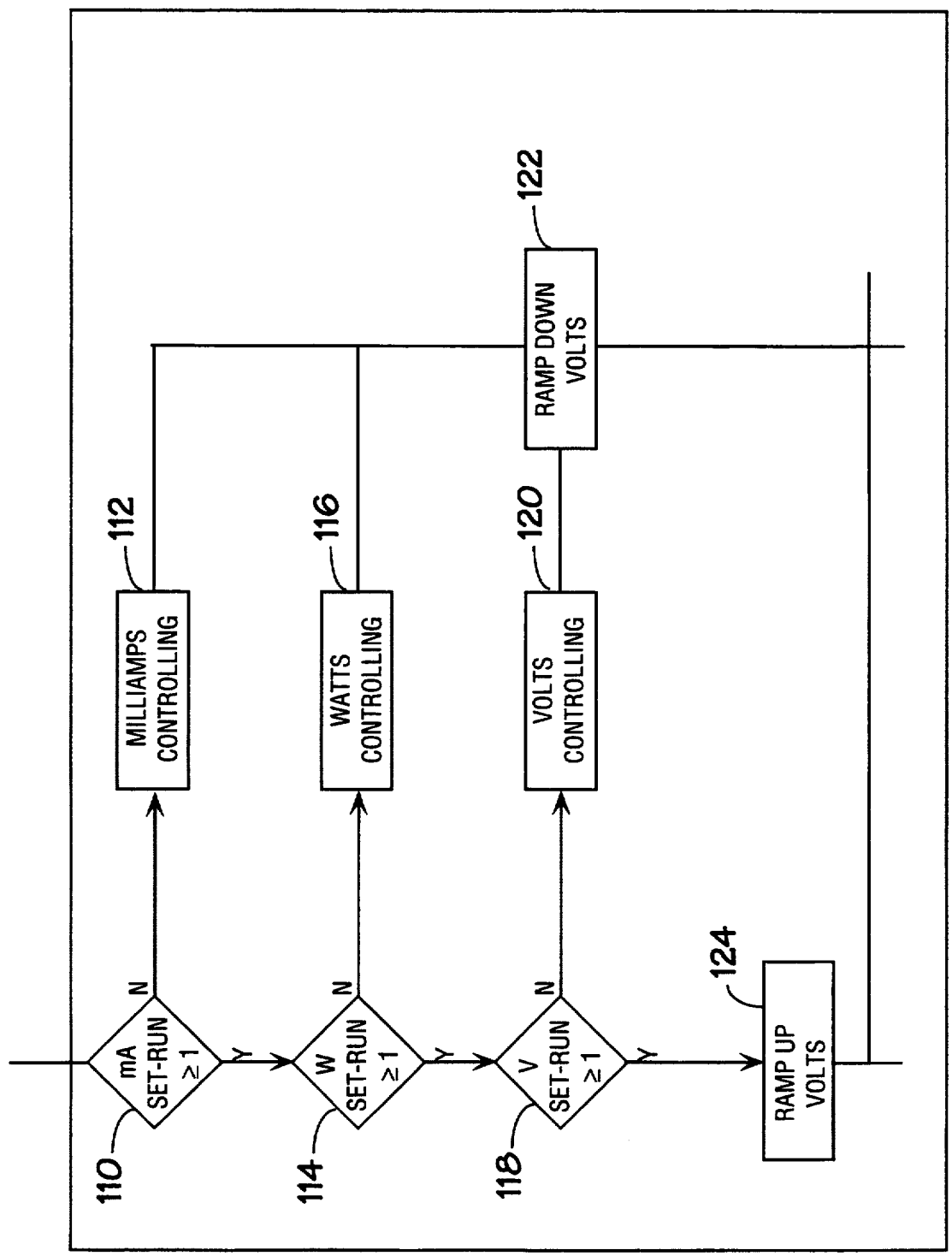
FIG. 3 is a computer program flow chart for adjusting the run value of the controlling parameter in accordance with the computer program flow chart in FIG. 2.

With reference to FIGS. 2 and 3, in one embodiment of the present invention, the control software originates of step 60 Begin and step 62, Clear Flag A and Clear Flag B, then step 64 determines whether high voltage (HV) switch A is on. If HV switch A is on, step 66 sets Flag A, but step 68 clears Flag A if HV switch A is not on. Likewise, step 70 determines whether HV switch B is on. Step 72 sets Flag B if HV switch B is on, and step 74 clears Flag B if it is not. Then, step 76 determines whether side A or side B is in SET mode. If side A is in SET mode, step 78 allows the input of side A parameter values, and step 82 updates the display. If side B is in SET mode, step 80 allows the input of side B parameter values, and step 82 updates the display. However, if neither side A nor side B is in SET mode, then the input steps are bypassed, and step 82 updates the display. Next, step 84 determines whether Flag A is set. If Flag A is set, then step 86 monitors the run and set parameter values inputted above, step 88 adjusts the run value for the controlling parameter, and step 90 determines whether the volt-hour or time parameters have expired for side A. If either one has expired, step 92 clears Flag A and shuts down side A. Then, regardless of whether the volt-hour or time parameters have expired, step 94 determines whether Flag B is set. If Flag B is set, step 96 monitors the run and set parameter values inputted above. Thus, the present invention integrates the control of two independent applications in one efficient, multi-outlet power supply. Step 98 adjusts the run value for the controlling parameter, and step 100 determines whether the volt-hour or time parameters have expired for side B. If Flag B is not set or if either volt-hours or time has expired, then step 102 clears Flag B and shuts down side B. Then, the software returns to step 64 and proceeds to control both sides of the power supply. Consequently, another advantageous feature of the present invention is the ability to adjust SET parameter values for an application in RUN mode when the software returns to step 76.

FIG. 3 illustrates the preferred internal operations of steps 88 and 98 with volts as the initial controlling parameter. First, step 110 determines whether the set value minus the run value for milliamps is greater than or equal to one. If it is not, step 112 will cause the program to cross over with milliamps controlling, and step 122 will ramp down the volts value. However, if the set value minus the run value for milliamps is greater than one, then step 114 determines whether the set value minus the run value for watts is greater than or equal to one. If it is not, step 116 causes the software to cross over with watts controlling, and step 122 ramps down the run value for volts. When the set value minus the run value for watts is greater than or equal to one, step 118 determines whether the set value minus the run value for volts is greater than or equal to one. If it is greater than or equal to one, step 124 will ramp up the run value for volts. If it is not greater than or equal to one, step 120 will indicate that voltage is the controlling parameter, and step 122 will ramp down the run value for volts. In slightly more complex embodiments, there may be intermediate steps which, for example, bypass the ramping steps if the difference between set and run values for the controlling parameter is less than or equal to one.

Figure 4:
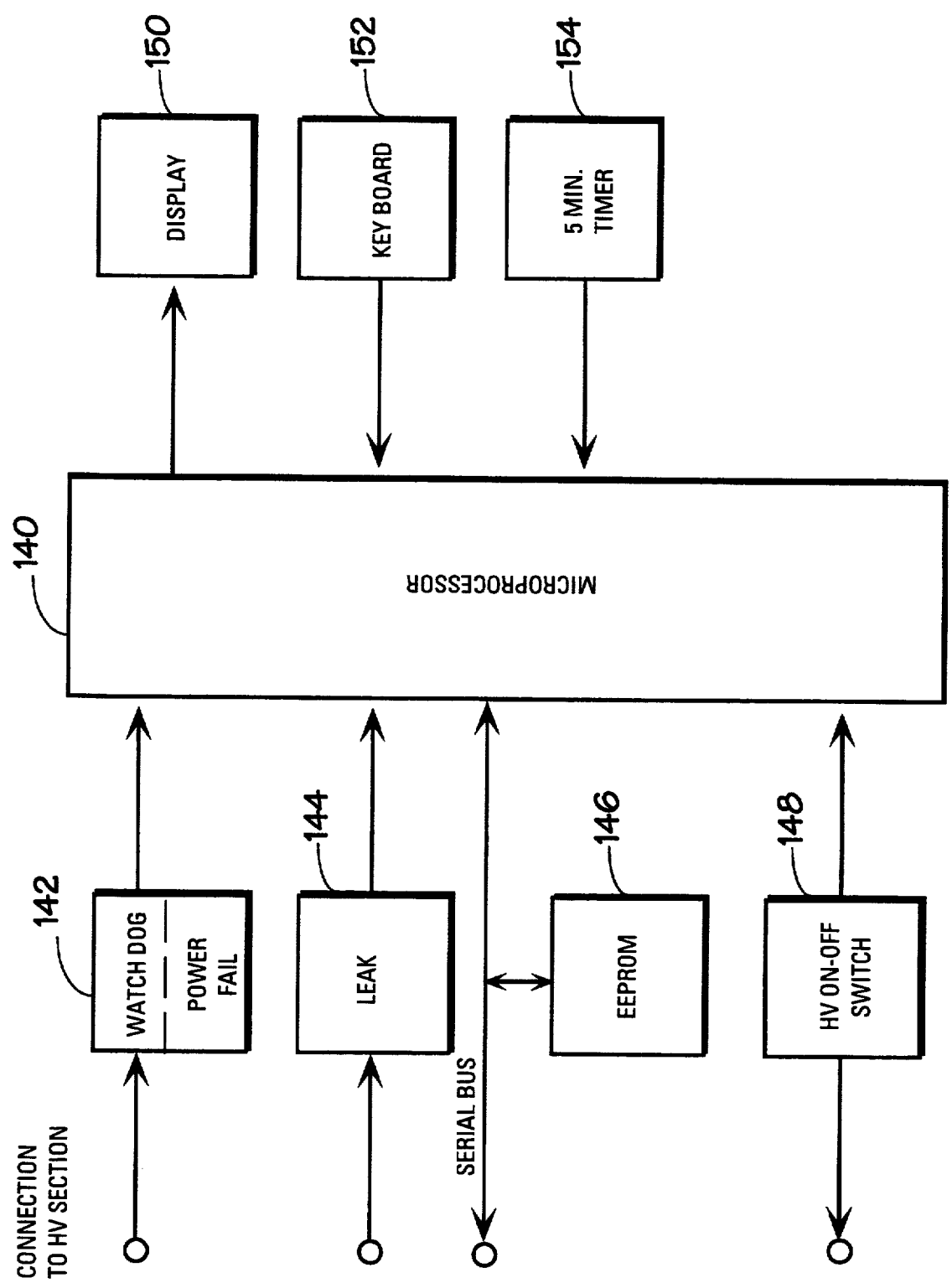
Figure 5:
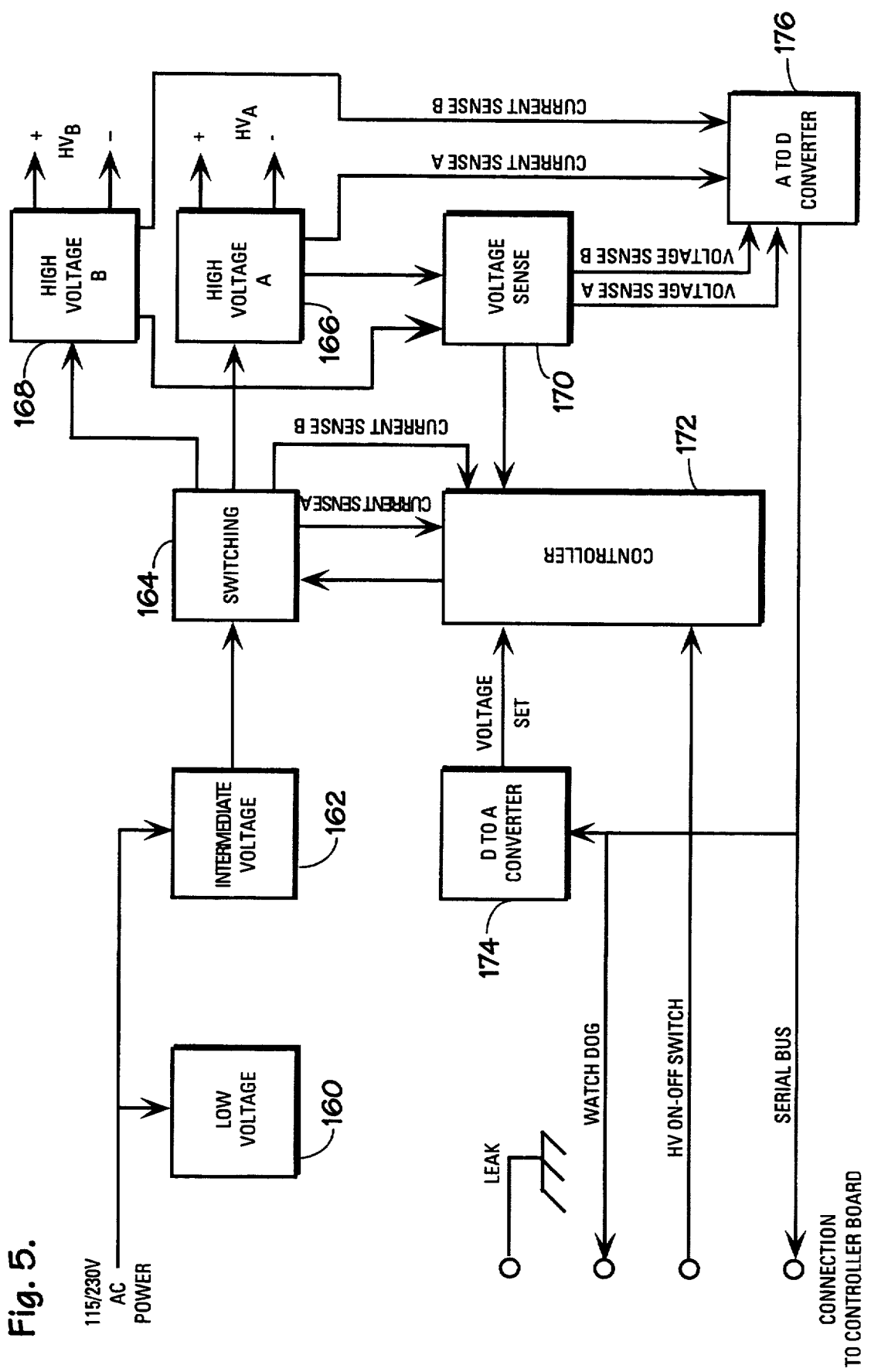

Referring now to FIGS. 4 and 5, the controller board contains the microprocessor control circuit which handles the input and output data for both sides of the power supply. Microprocessor 140 controls all of the input and output functions required to operate both sides of dual power supply 10. A suitable microprocessor chip is part number 87C51FA manufactured by Intel Corporation, but any number of similar computer chips will adequately perform the functions of microprocessor 140. Supervisory circuit 142 monitors the conventional watchdog and power fail signals. Conventional leak detection circuit 144, keyboard 152, and 5-minute timer 154 are also inputs to microprocessor 140. Electrically erasable programmable read-only memory (EEPROM) chip 146, a chip of the type well known to those skilled in the art, is electrically coupled with microprocessor 140 along the serial bus. EEPROM 146 stores data at power down, including the set parameters for side A and side B applications, parameter calibration factors, and cumulative time and volt-hour values for applications currently running. The HV on-off switch 148 inputs to both microprocessor 140 and to the HV section shown in FIG. 5. Display 150 is an output from microprocessor 140.

The high voltage section generates low, intermediate, and high voltages in the course of providing the integrated power supply of the present invention. First, AC power enters the unit at low voltage circuit 160 and intermediate voltage circuit 162. The low voltage circuit 160 powers the displays and the internal integrated circuit devices. Then intermediate voltage circuit 162 drives switching circuit 164, which produces both high voltage A 166 and high voltage B 168. For each side of power supply 10, a resistor (not shown) in switching circuit 164 senses current flow and inputs this current sense voltage to controller 172. Voltage dividers sense the voltage at output 16 and output 18 and feed this information to voltage sense circuit 170. One output of voltage sense circuit 170 goes to analog to digital (A to D) converter 176 so that the microprocessor can monitor the output. The other output from voltage sense circuit 170 goes to controller 172 so that the controller chip can adjust its output drive to hold the high voltage at the set value. The current flow in the primary of the high voltage transformer is sensed by the current sense transformer, and, if it exceeds a set value, the controller will shut down the high voltage section. This current sense is inputted to A to D converter 176. D to A converter 174 is a digital to analog conversion chip that supplies controller 172 with the set parameter values.

In operation, A Select switch 34 is depressed to place side A in SET mode. LED 36 will light, indicating that side A is in SET mode. Then program switch 20 is depressed to select side A, and the increase button 42 is depressed a number of times corresponding to the desired program number, A1 through A5, on side A. Volts switch 22 is depressed to select the value for voltage in conjunction with increase button 42 and decrease button 44. Similarly, the desired values for milliamps, watts, time, and volt-hours may be selected using the parameter switch in conjunction with the increase button 42 and decrease button 44. The link/stop switch 32 allows two programs to automatically run consecutively when link is selected, but if switch 32 is depressed again, then the next program will not be linked to the present one. Linking programs consecutively allows the dual power supply to operate for extended periods of time without undue delay or human supervision. The selected value for each of the above parameters is displayed on display 14 as shown in FIG. 1a.

Before running this program, the appliance, or gel, may be electrically coupled to output 16 by connecting the positive terminal to one buffer of the gel and the negative terminal to the other buffer. Then the program may be run by depressing Run A switch 46. Also, display 14 displays actual values in RUN mode rather than the set values it displays in SET mode.

FIG. 2 illustrates the operation of the embodiment of the present invention shown in FIG. 1a. Step 76 determines if either side A or B side is in SET mode. Only one side of power supply 10 nay be in SET mode at a time. Step 84 determines whether side A is in RUN mode, and step 94 determines whether side B is in RUN mode. The present invention makes it possible for both side A and side B to be in RUN mode at the same time, or one side may be in RUN mode by itself. If the set value for volt-hours or time expires for one side, then the flag for that side will be cleared, and that side will be shut down. Thus, while applications may run concurrently on side A and side B, they need not begin and end at the same time.

When side A is in RUN mode, step 86 monitors both run and set parameter values for side A. Step 88 adjusts the run value for the controlling parameter after comparing run and set parameter values for side A. FIG. 3 more particularly illustrates the operation of step 88. In a preferred embodiment, volts, milliamps, or watts may be controlling. That is, the controlling parameter remains substantially constant (once it approaches its set value) so long as the other parameters do not exceed their set values. For instance, if volts is controlling and the run value of milliamps exceeds its set value, milliamps becomes the controlling parameter and the run value of volts is ramped down in order to also lower the run value of milliamps. Even if the run values for milliamps and watts never reach their set values, steps 118 and 124 compare run and set values for volts, the controlling parameter in this example, as it climbs toward the set value and then as it maintains the run value at a substantially constant level. As shown in FIG. 3, volts is preferably the only parameter that is actually ramped although milliamps or watts may be the controlling or limiting parameter for the purposes of the application.

Additionally, for step 98, the comparison of set and run values for watts includes comparing the sum of the run values for side A and side B, and comparing that value to the maximum watts capacity of power supply 10. If, for example, there is no application running on side A, then the sum of run values for watts will equal the run value for watts on side B. However, if applications are running on both sides, A and B, and the sum of the run values for watts meets or exceeds the unit's maximum watts capacity, then watts will become the controlling parameter on side B. Accordingly, the constant watts value on side B will be limited to the difference between the unit's maximum watts capacity and the run value for watts on side A. The present invention contemplates the summing of like parameter values on side A and side B within step 88 instead of or in addition to step 98.

It is to be understood that while certain forms of the present invention have been illustrated and described it is not to be limited thereto except insofar as such limitations are included in the following claims.

Having thus described the invention, what is claimed is:

1. A method of controlling a plurality of electrical power supplies for applications in a laboratory, said method comprising the steps of:
   providing at least two substantially independent high voltage outputs;
   selecting a first set of parameter values corresponding to a first application;

electrically coupling the first application with a first one of said high voltage outputs;

selecting a second set of parameter values corresponding to a second application;

electrically coupling the second application with a second one of said high voltage outputs;

monitoring the actual value of at least one parameter for each of said first and second applications;

comparing the sum of the monitored actual values of at least one like parameter with a corresponding maximum parameter value; and adjusting the actual value of a first monitored parameter for each of said first and second applications to maintain said monitored actual parameter values within corresponding selected parameter values and within said corresponding maximum parameter value.

2. A method as set forth in claim 1, further comprising the step of adjusting the actual value of a second monitored parameter for said first application to maintain said monitored actual parameter values within said corresponding selected parameter values and within said corresponding maximum parameter value, then repeating said monitoring step.

3. A method as set forth in claim 1, further comprising the step of modifying at least one of said selected parameter values corresponding to an electrically coupled application subsequent to said adjusting step, then repeating said monitoring and adjusting steps.

4. A method as set forth in claim 1, further comprising the step of displaying the first set of selected parameter values corresponding to the first application.

5. A method as set forth in claim 4, further comprising the step of displaying the actual value of at least one parameter for said first application subsequent to said monitoring step.

6. A method of controlling a plurality of electrical power supplies for electrophoresis applications, said method comprising the steps of:

providing at least two substantially independent high voltage outputs;

providing at least two electrophoresis applications;

selecting a first set of parameter values corresponding to a first electrophoresis application;

electrically coupling the first electrophoresis application with a first one of said high voltage outputs;

selecting a second set of parameter values corresponding to a second electrophoresis application;

electrically coupling the second electrophoresis application with a second one of said high voltage outputs;

monitoring the actual value of at least one parameter for each of said first and second applications at substantially the same time;

selecting a controlling parameter for each of said first and second applications, wherein said controlling parameter is a monitored parameter; and adjusting the actual value of the controlling parameter for each of said first and second applications to maintain said monitored actual parameter values within the corresponding selected parameter values.

7. A method as set forth in claim 6, further comprising the step of comparing the sum of the monitored actual values of at least one like parameter with a corresponding maximum parameter value and adjusting the actual value of the controlling parameter to maintain said sum of like parameter values within said maximum value.

8. A method as set forth in claim 6, further comprising the step of converting to a new controlling parameter for said first application subsequent to said adjusting step, then repeating said monitoring and adjusting steps.

9. A method as set forth in claim 6, further comprising the step of modifying at least one of said selected parameter values corresponding to said first electrically coupled application subsequent to said adjusting step, then repeating said monitoring and adjusting steps.

10. A method as set forth in claim 6, further comprising the step of displaying the first set of selected parameter values corresponding to the first application.

11. A method as set forth in claim 10, further comprising the step of displaying actual parameter values for each electrically coupled application subsequent to said monitoring step.

12. An apparatus for supplying power to appliances in a laboratory, said apparatus comprising:

a first power supply;

an outlet for coupling a first laboratory appliance to said first power supply;

a second power supply;

an outlet for coupling a second laboratory appliance to said second power supply;

unitary means for monitoring actual parameter values of the power supplied to each of said first and second laboratory appliances at substantially the same time; and means for adjusting one of said actual parameter values for each of said first and second laboratory appliances to maintain said monitored actual parameter values within a set of corresponding selected parameter values for each of said first and second laboratory appliances.

13. An apparatus as set forth in claim 12, further comprising means for selecting a controlling parameter for each of said first and second appliances to maintain said actual parameter values within said corresponding selected values.

14. An apparatus as set forth in claim 13, further comprising means for converting to a new controlling parameter to maintain said actual parameter values within said corresponding selected values.

15. An apparatus as set forth in claim 13, wherein said adjusting means further comprises means for adjusting the controlling parameter of an appliance to maintain the sum of the actual values of at least one like parameter for each of said first and second laboratory appliances within a corresponding maximum parameter value.

16. An apparatus as set forth in claim 12, wherein said monitoring means further comprises means for comparing the sum of the actual values of at least one like parameter for each of said first and second laboratory appliances with a corresponding maximum parameter value.

17. An apparatus as set forth in claim 12, wherein said adjusting means further comprises means for modifying at least one selected parameter value from said set of selected parameter values corresponding to a laboratory appliance.

18. An apparatus as set forth in claim 12, further comprising means for displaying said actual parameter values and said selected parameter values for each of said first and second laboratory appliances.

19. An apparatus as set forth in claim 12, further comprising an outlet for coupling a third laboratory appliance to said first power supply.

* * * * *